United States Patent [19]
Puppolo

[11] Patent Number: 5,562,535
[45] Date of Patent: Oct. 8, 1996

[54] METHOD OF PROCESSING SHARK CARTILAGE

[76] Inventor: Celeste Puppolo, 8701 Bradford Rd., #1, Silver Spring, Md. 20901

[21] Appl. No.: 511,194

[22] Filed: Aug. 4, 1995

[51] Int. Cl.$^6$ .................................................. A22C 17/00
[52] U.S. Cl. ................................... 452/198; 452/135
[58] Field of Search .................................... 452/198, 135; 435/267

[56] References Cited

U.S. PATENT DOCUMENTS

| | | | |
|---|---|---|---|
| 3,895,106 | 7/1975 | Morrison | 424/180.1 |
| 4,350,682 | 9/1982 | Balassa | 424/64 |
| 4,448,718 | 5/1984 | Yannas et al. | 260/123.7 |
| 4,656,137 | 4/1987 | Balassa | 435/267 |
| 4,971,955 | 11/1990 | Soll et al. | 514/54 |
| 5,075,112 | 12/1991 | Lane | 424/434 |

*Primary Examiner*—Willis Little

[57] ABSTRACT

Raw shark cartilage is cleaned of all adhering tissues in organic solutions, ball-milled to fine semi-dry granules, and propelled into a drying chamber to impose sound waves upon the cartilage material so as to produce dehydrated shark cartilage at short exposure time and low temperature.

2 Claims, 3 Drawing Sheets

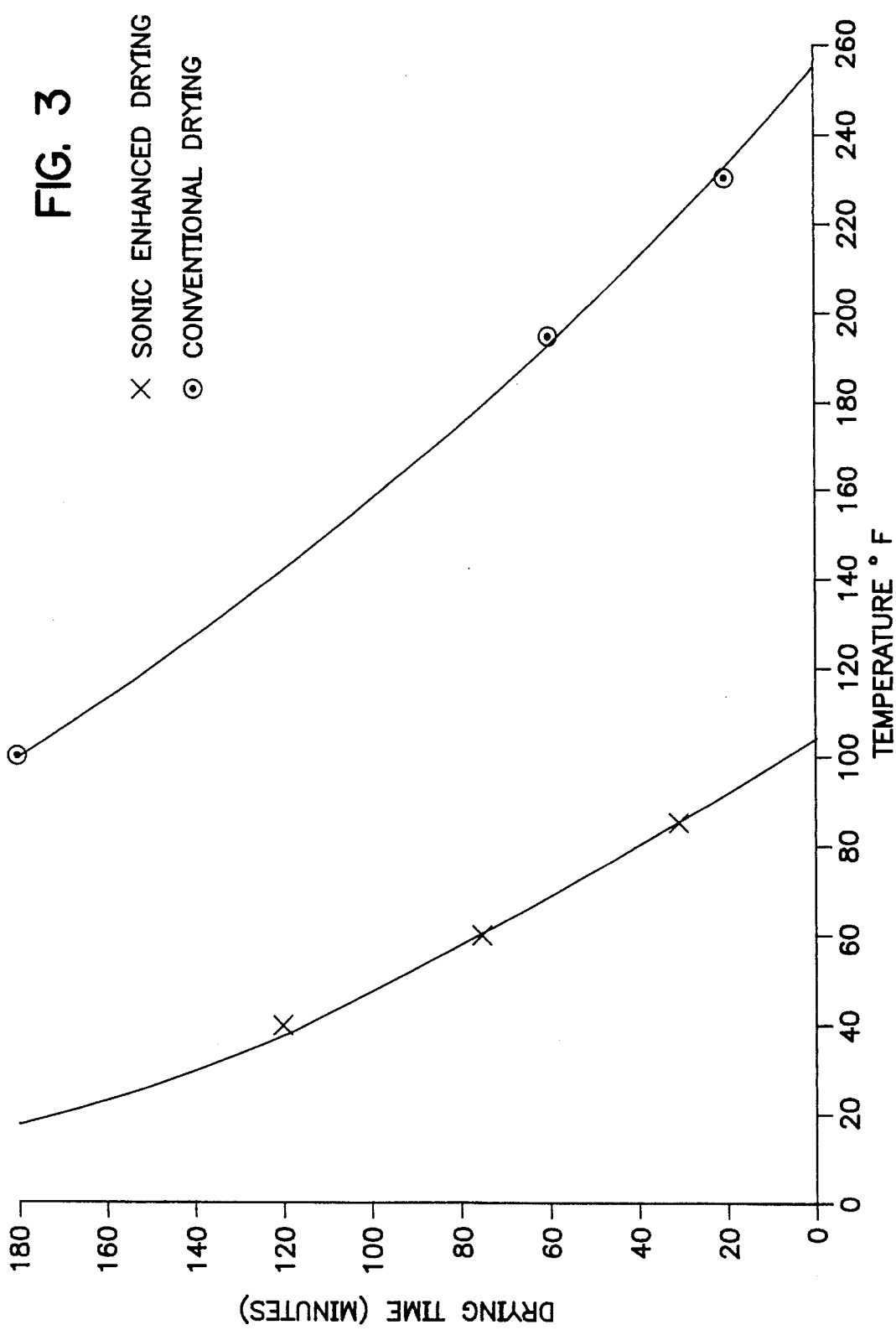

METHOD OF PROCESSING SHARK CARTILAGE

BACKGROUND OF THE INVENTION

This invention relates to a method of processing raw shark cartilage by sonic enhanced drying at temperatures and times that preserve the temperature-sensitive angiogenic inhibitor proteins found in shark cartilage.

Prior art methods for processing shark cartilage have included the use of convection and vacuum ovens, freeze drying techniques, and azeotropic extractions; all at temperatures which are high enough to cause the loss of significant amounts of the angiogenic inhibitor proteins.

It is an object of this invention to provide sonic enhanced drying of raw shark cartilage at lower temperatures and times than the prior art processes.

SUMMARY OF THE INVENTION

This invention uses sonic enhanced drying for the preservation of temperature-sensitive angiogenic inhibitor proteins in shark cartilage. Operating at 85° F., the sonic dryer propels at the speed of sound hydrated shark cartilage product into a drying chamber for complete dehydration. The dryer imposes sound waves upon cartilage material in the presence of heated air. The dehydrated product, dried at sonic speed with significantly lower temperature and exposure time, is spared potential denaturing of its biologically active protein, thus enhancing its theraputic value.

Disclosed is a method of preparing finely divided cartilage powder from raw cartilage including steps of preparing the raw cartilage prior to sonic enhanced drying which insures the preservation of temperature-sensitive angiogenic inhibitor proteins in the shark cartilage. The normal drying, pulverization, and sterilization processes with excessive heat as well as treatments using solvents or chemicals often denature the active protein in cartilage and render the protein and therefore the cartilage therapeutically valueless. Cartilage is more than 85% water and the way in which water is bound with the cartilage also makes drying difficult and costly under normal drying procedures.

BRIEF DESCRIPTION OF THE DRAWING

The drawing shows a known sonic drying apparatus usable for the method this invention.

Graph 1 compares shark cartilage yield for sonic enhanced drying according to the method of this invention compared with conventional drying.

Figure 1:
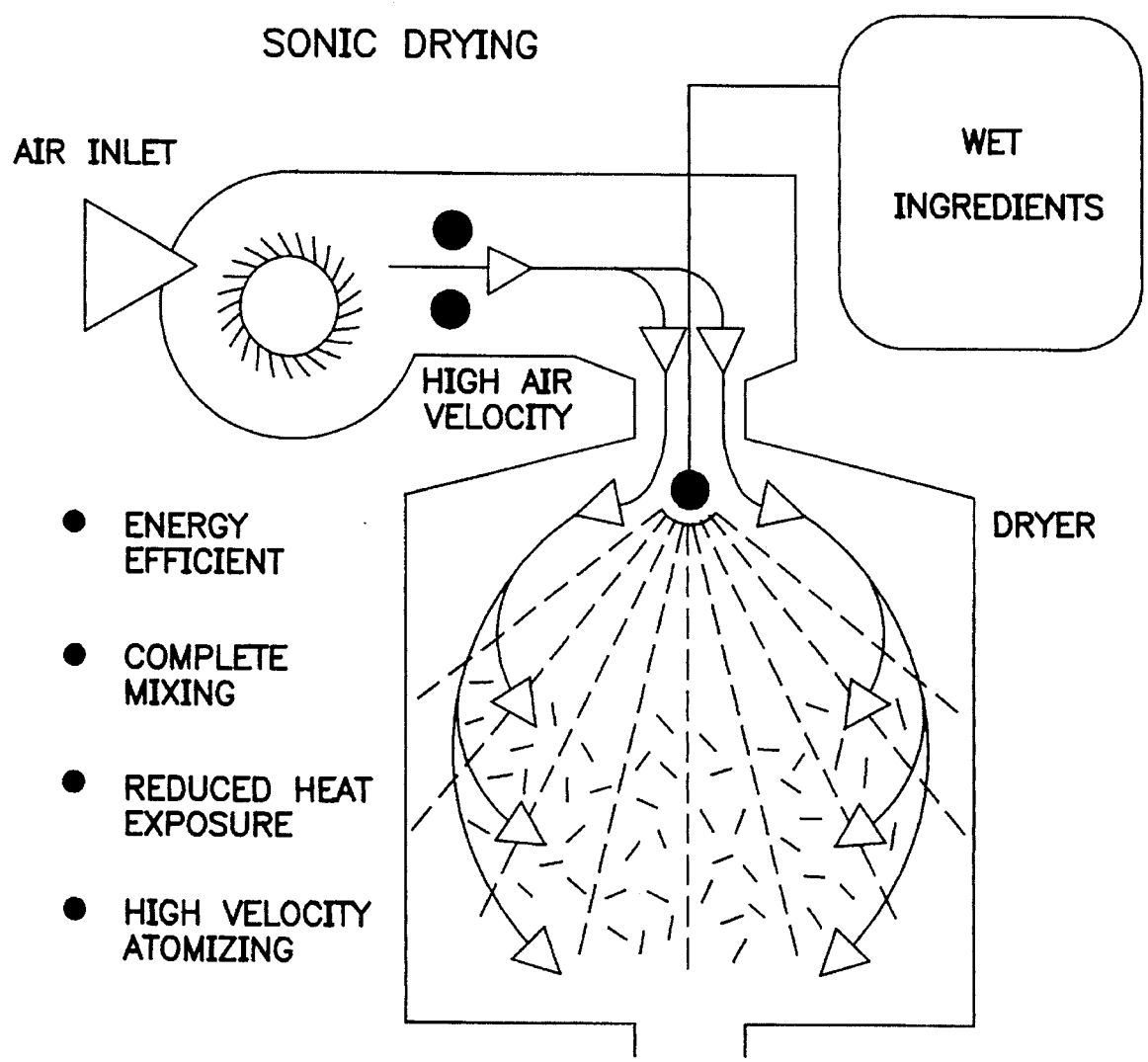
Figure 2:
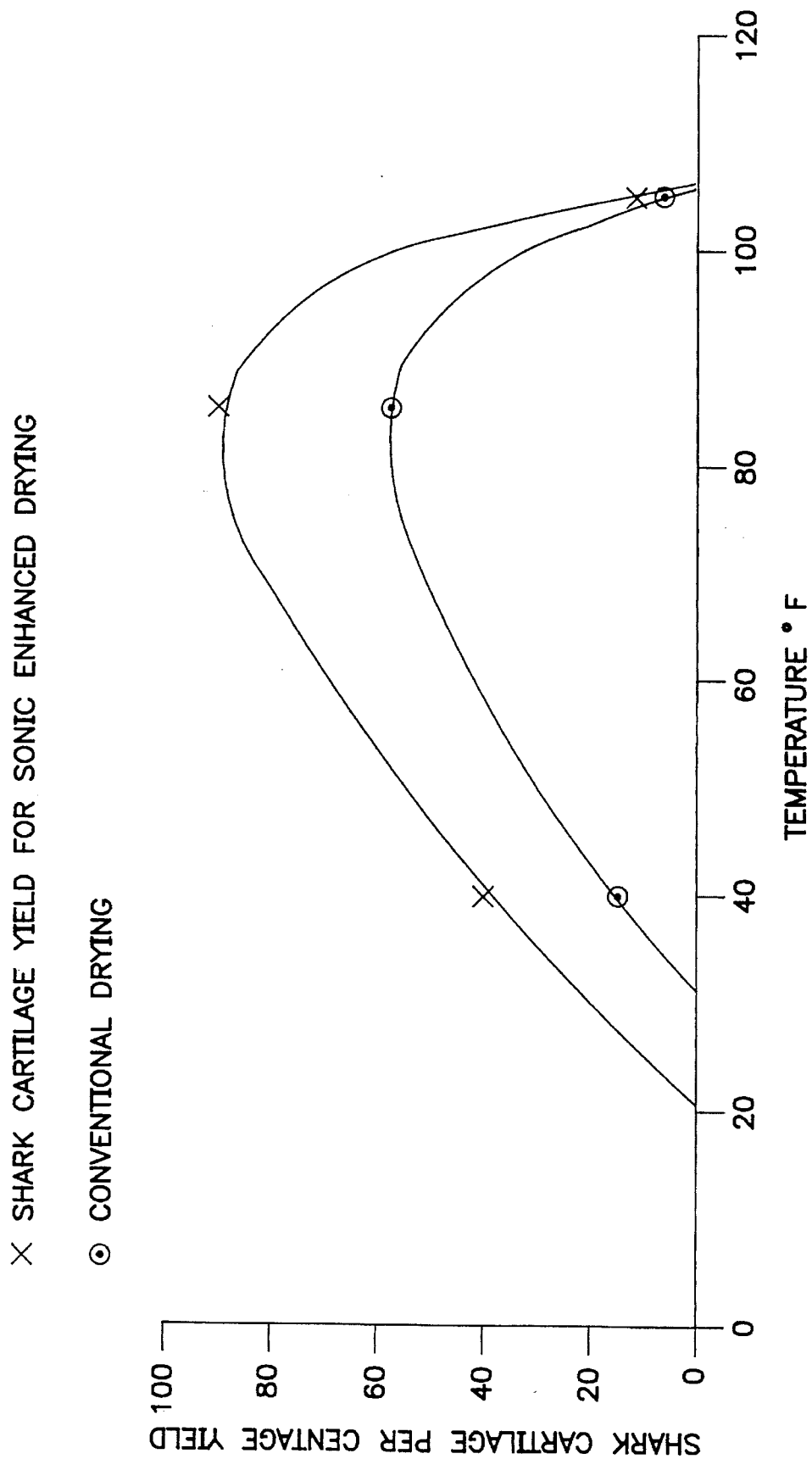

Graph 2 compares the drying times for sonic drying compared to conventional drying.

DETAILED DESCRIPTION OF THE INVENTION

The known sonic drying apparatus shown in the drawing is usable in the practice of the method of this invention.

Sonic enhanced drying forces liquid streams into a drying chamber at a speed nearing that of sound. This velocity allows the liquid to be dried at temperatures around 85° F. and it decreases the time the product is in the dryer. This new process improves upon the commonly used heat drying methods. Vital nutrients including proteins, vitamins, enzymes and chelated minerals are protected using sonic enhanced drying. Sonic enhanced drying mixes, homogenizes and atomizes the product. The powder dispenses evenly when used as a powder or powder in water solution.

Cartilage from skeletons of shark are used to prepare cartilage products. However, in the case of the shark, the spinal column is the most convenient tissue to obtain. Shark cartilage contains over 70% moisture and virtually no fat. Shark cartilage can be easily trimmed manually; however, an additional enzyme treatment is usually desirable to remove all adhering tissues.

To obtain a pure dry product, protein and fat should be removed from the trimmed cartilage. The protein is removed by proteolytic digestion. Digestion is accomplished using a solution containing a proteolytic enzyme which may be one or a combination of pepsin, or other enzymes in a dilute solution of hydrochloric or acetic acid that does not denature the enzymes. Granule sizes of 0.4 to 0.8 cm are preferred.

The next step (azeotropic extractions) is the removal of fat and water using a suitable solvent. Benzene, toluene, hexane and heptane are suitable solvents that form an azeotrope with water. Azeotropic extraction occurs when certain solvents form a mixture with another liquid, i.e. water. Sonic enhanced drying can be used to remove toluene and toluene-water azeotropes.

The semi-dry granules containing calcified powder layer are subjected to mechanical agitation such as milling in a ball mill with ceramic balls twice the weight of the cartilage granules for approximately 15–20 minutes or until the calcified layer becomes powdery. Desired particle of cartilage ground in the ball mill is 40 to 70 microns.

Removal of all solvent and all water is accomplished at 85° F. or lower. Sonic enhanced drying method reduces the time and temperature the shark cartilage exposed to heat. The diagram shows the elements of the drying process. After mixing and homogenizing the ingredients, the liquid is pressurized and forced through a tiny opening in the top of the main chamber at high speeds, thus atomizing the product. The atomized droplets are mixed with warm, high velocity air evaporating the water and solvents quickly and allowing dry particles to drop to the bottom of the chamber. The main purpose of the drying chamber is to provide intimate mixing of heated air with finely dispersed droplets.

The attached drawings show that less time required using sonic enhanced drying as compared to conventional drying resulting in a finer particle size and purer product of higher yield. The drawings also show that higher temperatures result in denaturing of the shark cartilage and lowering yield.

What is claimed is:

1. A method of processing shark cartilage comprising removing adhering tissues from raw shark cartilage, reducing said cartilage to hydrated granules, propelling said granules into a drying chamber and imposing sound waves onto said granules for short exposure times of about 30 minutes at low temperatures no greater than 85 ° F. to produce finely divided dehydrated shark cartilage.

2. The method of claim 1 wherein said removing adhering tissues is by digestion using an enzyme, and said reducing to granules is by ball-milling to about 40 to 70 microns.

* * * * *